United States Patent
Mergl et al.

(10) Patent No.: US 11,046,225 B2
(45) Date of Patent: Jun. 29, 2021

(54) METHOD FOR ACTIVATING MASSAGE UNITS IN A SEAT, CONTROL DEVICE FOR CARRYING OUT SAID METHOD, AND SEAT ARRANGEMENT

(71) Applicant: Brose Fahrzeugteile GmbH & Co. Kommanditgesellschaft, Coburg, Coburg (DE)

(72) Inventors: Christian Mergl, Zeil/Main (DE); Wojciech Falinski, Coburg (DE); Christian Karl, Coburg (DE); Martin Juergenliemk, Untersiemau (DE); Wolfgang Uebel, Weitramsdorf (DE); Christian Herrmann, Coburg (DE); Florian Pohl, Ebersdorf (DE)

(73) Assignee: Brose Fahrzeugteile SE & Co. KG (Coburg), Coburg (DE)

( * ) Notice: Subject to any disclaimer, the term of this patent is extended or adjusted under 35 U.S.C. 154(b) by 0 days.

(21) Appl. No.: 15/751,089

(22) PCT Filed: Mar. 23, 2016

(86) PCT No.: PCT/EP2016/056388
§ 371 (c)(1),
(2) Date: Feb. 7, 2018

(87) PCT Pub. No.: WO2017/025204
PCT Pub. Date: Feb. 16, 2017

(65) Prior Publication Data
US 2020/0139870 A1    May 7, 2020

(30) Foreign Application Priority Data
Aug. 7, 2015  (DE) .......................... 102015215171.9

(51) Int. Cl.
*A61M 21/02*      (2006.01)
*G06F 3/16*       (2006.01)
(Continued)

(52) U.S. Cl.
CPC ............. *B60N 2/976* (2018.02); *A61M 21/02* (2013.01); *G06F 3/165* (2013.01); *H04R 1/025* (2013.01);
(Continued)

(58) Field of Classification Search
CPC .......... B60N 2/976; H04R 3/00; H04R 1/025; H04R 2499/13; A61M 21/02; A61M 2021/0022; A61M 2021/0027; G06F 3/165
See application file for complete search history.

(56) References Cited

U.S. PATENT DOCUMENTS 5,951,500 A * 9/1999 Cutler ...................... A61H 1/00
                                                            601/46
6,027,463 A * 2/2000 Moriyasu ........... A61H 23/0236
                                                            601/46
(Continued)

FOREIGN PATENT DOCUMENTS

CN         2782084       5/2006
CN       201179183 Y    1/2009
(Continued)

OTHER PUBLICATIONS

International Search Report for International Application No. PCT/EP2016/056388 (dated Jul. 20, 2016).
(Continued)

*Primary Examiner* — Rodney A Butler
(74) *Attorney, Agent, or Firm* — Renner, Otto, Boisselle & Sklar, LLP

(57) ABSTRACT

A method for activating massage units in a seat, a control device for carrying out the method, and seat arrangement are (Continued)

described. One method for activating massage units in a seat, in particular in a vehicle seat, includes playing back an acoustic entertainment signal, in particular a piece of music, by means of a playback device, in particular an entertainment system of a vehicle. The method further includes controlling massage units integrated in the seat based on the acoustic entertainment signal by means of a control device.

18 Claims, 16 Drawing Sheets

(51) Int. Cl.
*H04R 1/02* (2006.01)
*H04R 3/00* (2006.01)
*B60N 2/90* (2018.01)
*A61M 21/00* (2006.01)

(52) U.S. Cl.
CPC ....... *H04R 3/00* (2013.01); *A61M 2021/0022* (2013.01); *A61M 2021/0027* (2013.01); *H04R 2499/13* (2013.01)

(56) References Cited

U.S. PATENT DOCUMENTS

| | | | |
|---|---|---|---|
| 6,087,942 | A | 7/2000 | Sleichter, III et al. |
| 7,039,207 | B1 | 5/2006 | Elrod et al. |
| 2002/0107458 | A1 | 8/2002 | Flick et al. |
| 2004/0097851 | A1* | 5/2004 | Inada ............... A61H 23/0254 601/47 |
| 2006/0217644 | A1 | 9/2006 | Ozaki et al. |
| 2012/0143108 | A1* | 6/2012 | Bocsanyi ............. F15B 13/081 601/148 |
| 2015/0008710 | A1 | 1/2015 | Young et al. |
| 2016/0354026 | A1* | 12/2016 | Zohar .................... B60N 2/976 |
| 2019/0077289 | A1 | 3/2019 | Mergl et al. |

FOREIGN PATENT DOCUMENTS

| | | | |
|---|---|---|---|
| CN | 202446462 | | 9/2012 |
| CN | 202686043 | U | 1/2013 |
| CN | 203020117 | U | 6/2013 |
| CN | 204367947 | U | 6/2015 |
| DE | 43 31 663 | C1 | 3/1995 |
| DE | 297 05 530 | U1 | 5/1997 |
| DE | 10 2007 051 759 | A1 | 5/2009 |
| DE | 10 2009 008 421 | A1 | 10/2009 |
| DE | 10 2009 031 331 | A1 | 8/2010 |
| DE | 10 2009 022955 | A1 | 12/2010 |
| DE | 10 2009 033041 | A1 | 1/2011 |
| DE | 102009033041 | A1 * | 1/2011 ............. B60N 2/976 |
| DE | 10 2011 015532 | A1 | 10/2012 |
| DE | 10 2013 216885 | A1 | 2/2015 |
| DE | 10 2015 007 578 | A1 | 12/2015 |
| DE | 10 2014 216 161 | A1 | 2/2016 |
| EP | 1 350 502 | A1 | 10/2003 |
| JP | 53-110208 | | 9/1978 |
| JP | 9117481 | | 5/1997 |
| JP | 2010-011923 | | 1/2010 |
| JP | 2014-168600 | | 9/2014 |
| JP | 2007-160129 | | 6/2019 |
| KR | 10-2007-0070201 | | 7/2007 |
| KR | 10-2012-0136173 | | 12/2012 |
| WO | WO 2017/025403 | A1 | 2/2017 |

OTHER PUBLICATIONS

Research Report for German Application No. 10 2015 215 171.9 (dated May 30, 2016).
Notification in accordance with Article 94 (3) EPO for European Application Serial No. 16 711 301.8 (dated May 12, 2020).
Decision of Refusal for Japanese Application Serial No. 2018-526296 (dated Nov. 14, 2019).
Notice of Preliminary Rejection for Korean Application Serial No. 10-2018-7006549 (dated Jun. 11, 2019).
First Office Action for Japanese Application Serial No. 2018-526296 (dated Mar. 28, 2019).
Office Action for Chinese Patent Application Serial No. 201680056605.X (dated Dec. 2, 2019).
International Search Report for International Application No. PCT/EP2016/068520 (dated Oct. 25, 2016).
Search Report for German Patent Application Serial No. 10 2015 215 170.0 (dated Jun. 2, 2016).
Second Office Action for corresponding Chinese Application No. 201680046565.0 dated Apr. 16, 2021.

* cited by examiner

METHOD FOR ACTIVATING MASSAGE UNITS IN A SEAT, CONTROL DEVICE FOR CARRYING OUT SAID METHOD, AND SEAT ARRANGEMENT

FIELD OF THE INVENTION

The present invention relates to a method for activating massage units in a seat, to a control device for carrying out said method, and to a corresponding seat arrangement.

TECHNICAL BACKGROUND

Methods are known which provide activation and deactivation, or playback, of a fixed, specified program sequence in order to activate massage units in a seat.

DE 297 05530 U1 describes a vehicle seat in which oscillating heads are integrated, the drive frequency of which heads can be set at different levels or in a continuously variable manner by a corresponding user input. Control of this kind provides only monotonous massage sequences, however.

DE 43 31 663 C1 describes a control apparatus which activates both the position-adjusting and contour-adjusting means of a vehicle seat. Said apparatus comprises a memory unit, in which activation programs for said means can be stored. The contour-adjustment means are activated simultaneously by the control apparatus in a predeterminable temporal sequence in order to initiate a massage and gymnastics program. The disadvantages of programs of this kind become clear to a user relatively quickly.

SUMMARY OF THE INVENTION

In view of the above, the aim of the present invention is to specify an improved method for activating massage units in a seat.

This aim is achieved according to the invention by a method having the features of claim 1 and/or by a control device having the features of claim 14 and/or by a seat arrangement having the features of claim 15.

Accordingly, there is provided:

A method for activating massage units in a seat, in particular in a vehicle seat, comprising the following steps: playing back an acoustic entertainment signal, in particular a piece of music, by means of a playback device, in particular an entertainment system of a vehicle; controlling massage units integrated in the seat based on the acoustic entertainment signal by means of a control device.

a control device for controlling massage units in a seat, in particular in a vehicle seat, which device is designed to convert an entertainment signal into at least one output signal that activates the massage units, and to activate the massage units in accordance with a method according to the invention.

a seat arrangement for carrying out a method according to the invention, comprising: a seat, in particular a vehicle seat, having a number of integrated massage units; a playback device, in particular an entertainment system of a vehicle, for playing back an acoustic entertainment signal; a control device coupled to the playback device for controlling the massage units, which is designed to convert the entertainment signal into at least one output signal that activates the massage units, which output signal changes based on the entertainment signal.

The concept forming the basis of the present invention consists in using a primary audio signal (acoustic entertainment signal) that is provided to an occupant for entertainment, in particular a piece of music, as an input variable for a control device in order to control massage units integrated in a seat.

In this manner, the invention makes it possible to create a completely new massage experience that can be provided by a vehicle seat, in which experience any variety of coordinated acoustic and tactile stimuli can be simultaneously set. A massage system can thus advantageously be used for other vehicle applications according to the invention.

If music is used as the primary entertainment signal in this case, the experience of listening to the music is enhanced by the massage given by the seat. According to the invention, the music can also be perceived by an occupant, in a tactile manner, in the form of a back and/or buttocks and/or neck and/or head massage, in particular over the majority of the body, by means of the massage units integrated in the seat. Overall, the music is thus experienced more intensely.

In addition, if the music is simultaneously output over speakers, the massage provided by the massage units is also experienced more intensely on account of the acoustic stimuli set with the music.

Since the acoustic and tactile stimuli are coordinated, there is overall a more intense experience according to the invention than if the massage and the music run independently of one another.

In addition, the program is unknown and is not "boring", since the program sequence can be varied in any desired manner by playing different music.

In particular, according to the invention, the entertainment system of a vehicle, optionally designed as an infotainment system, is coupled to the massage function of a vehicle seat.

An extractor may also be provided for extracting the entertainment signal from the playback device. A digital transmission of the entertainment signal from the playback device to the control device is also possible. The extracted or transmitted entertainment signal is then used as an input variable for the control device.

A number of massage units can indicate a singular number or a plural.

The method according to the invention can be provided in addition to known activations of massage units, in particular as an additional function.

Advantageous embodiments and developments will become apparent from the additional dependent claims and from the description with reference to the figures in the drawings.

According to one embodiment, the acoustic entertainment signal is broken down into predetermined frequency ranges. In the process, at least one predetermined frequency range of the acoustic entertainment signal is converted into an output signal for at least one massage unit. Thus, according to the invention, predetermined frequency ranges or also only one predetermined frequency range can be used to control massage units integrated in a seat. The predetermined frequency range(s) can be adapted to the type or genre of music. Advantageously, the frequency range which is the best match for the music and/or is most suitable for being translated into a massage is used.

In addition, one development provides for amplification and selection of different frequency ranges that is in both cases adapted to the type of entertainment signal, for example the type or genre of music in the case of music. In this way, for example in the case of techno or classical music as the entertainment signal, the massage units can thus be activated in a manner that is adapted to said music, and the experience of listening to the music in question is enhanced by the massage, which is adapted to the type of music, given by the seat.

According to one embodiment, different frequency ranges of the acoustic entertainment signal are each converted into an output signal and used to activate different massage units. Thus, the music can advantageously be perceived in a broken-down form. The massage is more varied and interesting as a result.

According to one embodiment, a plurality of massage units are arranged so as to be distributed over the sitting surface of the seat. The output signals associated with the different frequency ranges of the acoustic entertainment signal are in this case output in order to activate massage units that are arranged in different places. All frequencies can be converted into a massage, in particular a vibration massage, so as to be distributed over the various seat regions. For example, low frequencies, such as bass, for example having frequencies of from 80 to 100 Hz, can be converted into a massage in a lower region, in particular in seat upholstery or an underbody, and/or higher frequencies, such as medium and/or high frequencies, can be converted into a massage in an upper region, in particular a backrest. Distribution the other way around, or another kind of distribution, is also possible.

According to one embodiment, it is conceivable for the signals of a multi-channel signal, for example a stereo or digital multi-channel signal, such as a 5.1 signal, to be used for activation in individual regions of the seat. In particular, massage units can be activated in individual side regions in this way. The multi-channel signal can thus be reproduced by the massage by activating massage units that are arranged in different places. For example, a signal intended for a left-hand speaker of a stereo or 5.1 system can be used to activate massage units that are arranged on the left-hand side of the seat. The same can also be done for a right-hand region using the signal intended for a right-hand speaker. Divisions into more than two regions, for example 5.1 signals divided into six regions, are also conceivable.

According to one embodiment, only some of the massage units integrated in the seat are activated by means of the output signal based on the entertainment signal. Accordingly, not all of the massage units of a seat or seat region have to be subjected to a massage or vibration controlled by the acoustic entertainment signal. For example, a seat user himself can choose the regions which are intended to be massaged by the massage units, for example the back or legs. Instead, the other massage units can be idle, or a conventional massage program or a constant massage or vibration can be active. In a further embodiment, all of the massage units of a seat or seat region are provided with a massage or vibration controlled by the acoustic entertainment signal.

According to one development, constantly alternating motors can be activated in succession. Preferably, the changes are such or are carried out such that they are imperceptible to an occupant, i.e. a person sitting on the seat. Thus, at any given time, only some of the massage units are activated simultaneously. For this purpose, a control apparatus distributes levels for activating the motors of the massage units such that not all the motors of the massage units provided in a seat simultaneously react to a level of the entertainment signal. Instead, the motors can alternate, and are thus stopped, in an alternating manner, for a predetermined period of time, in particular in order to cool the motors of the massage units. In the process, the motors are preferably activated such that the cooling phases of individual motors can be integrated in a massage program that is based on the entertainment signal, meaning that the alternation of the motors is imperceptible to the occupant. There is thus an even massage effect, despite the alternation.

According to one embodiment, the acoustic entertainment signal is used as an input variable for the activation irrespective of an output volume set on the playback device. Accordingly, it is also optionally possible for the acoustic entertainment signal not to be heard at all. For example, operating modes are thus possible in which, where music is the primary entertainment signal, songs can be guessed on the basis of the massage. For example, different songs can be selected by an occupant, in particular the driver or a passenger in the front seat, as the basis for a massage program. The songs can then be guessed by the other occupants of a vehicle, for example by one or more persons sitting on the back seats. An additional entertainment offering is thus advantageously provided. In a further embodiment or in an alternative mode, the intensity of the vibrations can also be controlled depending on the volume set on the playback device.

In yet another embodiment, for example in an electric car, an artificially generated engine noise can be used as the primary acoustic signal, which in this case is an entertainment signal. This can be used to activate the massage units irrespective of a volume of the engine noise that is played. The vibrations of an internal combustion engine can thus be imitated, for example. In addition, the filters for an additional playback of music can be adapted to a possible engine noise.

According to one embodiment, the intensity of the massage provided by the massage units can be set. In particular, for this purpose, the vibration intensity of the massage units can be set. Alternatively or additionally, the frequency band used can be set. In particular, for this purpose, the position and width, i.e. the nature of the different frequency ranges of the acoustic entertainment signal, which are converted into an output signal, can be set. The vibration frequency of the massage units can thus be set according to the wishes of the customer or operator. Alternatively or in addition, the distribution of the activated portion of the massage units can also be set. In particular, for this purpose, the position and number of the activated massage units can be set. A plurality of massage unit positions, for example the sitting surface or backrest surface, or the left-hand side and right-hand side thereof individually in each case, and the number of massage units in each case, can also be set. Preferably, the setting is in each case free setting. Advantageously, there is thus a wide range of setting possibilities in order to provide an individually adapted massage.

According to one embodiment, the acoustic entertainment signal is converted into a series of pulses for the activation of the massage units, in particular by pulse-width modulation (PWM), preferably by means of an individual high-side switch. Advantageously, a particularly simple, economical and cost-effective amplifier is used to activate the massage units, for example in the form of a class-D amplifier (PWM).

According to one embodiment, the dynamic profile of the acoustic entertainment signal is compressed or expanded for the activation. Both of these processes can also take place, in particular in stages. The compression is used in particular to limit the dynamic range of the acoustic entertainment signal. By means of the expansion, the dynamic range of the acoustic entertainment signal can be increased. For this purpose, for example a dynamic processor is provided, in particular a dynamic compressor for compressing and/or in particular a dynamic expander for expanding, which processor processes the primary entertainment signal accordingly. In particular, a reduction of low noise levels can be achieved by means of a dynamic expander as a continuous effect, whereas higher levels remain unaffected. Noise from the control, for example, can thus be excluded. Furthermore, a high noise level or level peaks, thus a pulse-like effect, can be attenuated advantageously by means of a dynamic compressor. Advantageously, the whole signal can thus be amplified, and in particular lower noise levels can be raised in the process, without this resulting in the massage units being overloaded.

According to one embodiment, the acoustic entertainment signal is fed into the playback device by means of an audio signal source, in particular a mobile audio signal source or a vehicle-internal audio signal source. This can also be an audio signal source that is integrated in a seat, or a vehicle-external audio signal source. The playback device is coupled to the audio signal source for this purpose. In the case of a mobile audio signal source, this can be realised by a connection cable or by wireless data transmission. In the case of a vehicle-internal audio signal source, this is preferably integrated in the entertainment system of the vehicle, and is in particular rigidly coupled thereto. In the case of a vehicle-external audio signal source, this can be for example a digital or analogue radio or television transmitter. In this case, the playback device has a corresponding receiver, in particular a tuner.

According to one embodiment, the massage units are activated so as to vibrate in frequency ranges in which they only bring about noise emissions which are externally imperceptible to persons other than those sitting on the seat in question, in particular other vehicle occupants. In particular, the massage units are in this case activated so as to vibrate in frequency ranges which do not constitute a resonance frequency of the structure of the vehicle seat. Preferably, these are frequencies which are damped to a great extent by the structure of the vehicle seat. Advantageously, there is thus no sound, or only sound that is below the threshold of perceptibility, caused by the vibration. Specific massage units can, in a targeted manner, also be excluded or adapted, for example adapted to a noise environment, or activated only if this is not to the detriment of a comfortable noise level. The vibration frequencies can also be adapted, in a tailored manner, to different massage units. For this purpose, for example only predetermined frequencies can be output in specific regions of the seat. In particular, for this purpose, the rotational speed of an unbalance motor can be restricted to predetermined ranges. The output of the predetermined frequencies can be selected so as to be adapted to the local damping that is provided at the relevant seat region, and/or to the weight of a person sitting on the seat.

According to one embodiment, the massage units are arranged and activated such that the vibration thereof covers or neutralises adjustment noise that is simultaneously generated by an electromotive seat adjustment. In particular, for this purpose, individual or different massage units can be provided, in terms of position, so as to be coupled in a compatible manner to an adjustment plane, in order to cover adjustment noise.

According to one embodiment, the control of the individual massage units can be selected so as to depend on the placement of individual seat components. In particular, these are seat components in which the massage units concerned are arranged. For example, the control can take place depending on how a lumbar support is set, in particular at a low level of vibration in the case of a lumbar support that is extended fully towards the front.

According to one embodiment, a speaker outputs the acoustic entertainment signal in parallel with the activation of the massage units. Thus, in particular in the case of music as the entertainment signal, the massage provided by the massage units can advantageously be experienced more intensely on account of the acoustic stimuli. The listening experience is also enhanced by the massage given by the seat. Music is thus also perceived by an occupant, in the form of a massage, by means of the massage units integrated in the seat. Overall, the music is thus experienced more intensely. Since the acoustic and tactile stimuli are coordinated, there is advantageously a more intense experience overall than if the massage runs without the music being output by a speaker.

According to one embodiment of a seat arrangement for carrying out a method according to the invention, the massage units are designed as unbalance motors that can be operated in various frequency ranges. Thus, the frequencies can advantageously be adapted. The unbalance motors are in particular unbalance step motors. Advantageously, the positions of the eccentric weight of each of the massage units can thus also be coordinated. In particular, synchronous vibration phases or specific spread patterns of the vibration can be produced. Additional functions are thus advantageously provided.

According to one embodiment of a seat arrangement, a rectifier element is arranged in the motor supply line or in a connection between the playback device and the control device. This can be a diode, in particular. Said diode can be inserted into an audio supply line of an amplifier, for example. The motor balance weight is thus not actively decelerated by a negative half wave. Advantageously, the power consumption of the motors, in particular unbalance motors, of the massage units is reduced, and the vibration effect is enhanced. In particular, either a rectifier element or a high-side switch can be provided.

The above embodiments and developments can be combined with one another as desired, where appropriate. In particular, the features of the method for activating massage units in a seat can be transferred to a control device for controlling massage units in a seat and/or can be combined with the features of a seat arrangement for carrying out said method, and vice versa. Further possible embodiments, developments and implementations of the invention also include combinations of features of the invention that have been previously described or are described in the following with respect to the embodiments, even if not explicitly mentioned. In particular, a person skilled in the art will also add individual aspects as improvements or additions to the relevant basic form of the present invention.

SUMMARY OF THE DRAWINGS

The present invention is explained below in greater detail with reference to the embodiments specified in the schematic figures of the drawings, in which.

The accompanying figures of the drawings are intended to provide further understanding of the embodiments of the invention. They illustrate embodiments and, together with the description, are used to explain principles and concepts of the invention. Other embodiments and many of the mentioned advantages will become apparent from the drawings. The elements of the drawings are not necessarily shown to scale relative to one another.

In the figures of the drawings, identical, functionally equivalent and equivalently operating elements, features and components are provided with the same reference signs in each case, unless stated otherwise.

DESCRIPTION OF EMBODIMENTS

Figure 1:
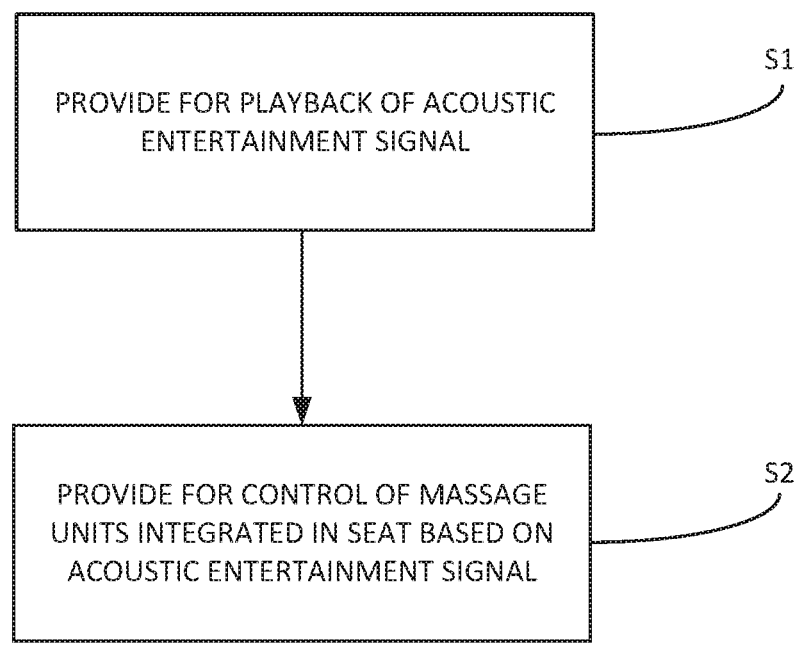
FIG. 1 is a flow diagram of one embodiment of the method according to the invention.

FIG. 1 is a flow diagram of one embodiment of the method according to the invention for activating massage units 102-1 to 102-n in a seat 103. In this case, the seat 103 can e.g. be a vehicle seat 103 in particular.

The method provides for the playback, S1, of an acoustic entertainment signal 104. The method further provides for the control S2 of massage units 102-1 to 102-n integrated in the seat 103 based on the acoustic entertainment signal 104.

The acoustic entertainment signal 104 may be for example a piece of music, which is played back by means of a playback device 105. In particular in a vehicle seat 103, thus the application of the method in a vehicle, the playback device 105 can be an entertainment system, e.g. a radio or CD player, of the relevant vehicle, or can be coupled thereto.

The massage units 102-1 to 102-n can be arranged so as to be distributed over the sitting surface of the seat 103. In this way, different frequency ranges of the acoustic entertainment signal 104 can be output as the output signal 107 in order to activate massage units 102-1 to 102-n that are arranged in different places. For example, higher frequency ranges of the acoustic entertainment signal 104 can be used in order to activate massage units 102-1 to 102-n in the shoulder and neck region, whereas low frequency ranges of the acoustic entertainment signal 104 can be used in order to activate massage units 102-1 to 102-n in the leg and buttocks region. It goes without saying that this allocation is merely exemplary and further variants are possible.

The frequencies can be allocated in a manner that does not depend only on their level. For example, the massage units 102-1 to 102-n can be activated so as to vibrate in frequency ranges in which they only bring about noise emissions which are externally imperceptible to persons other than those sitting on the seat 103 in question, in particular other vehicle occupants. In addition or alternatively, the massage units 102-1 to 102-n can be arranged and activated such that the vibration thereof or the noise generated thereby covers or neutralises adjustment noise that is generated by an electromotive seat adjustment.

In addition, during control S2, only some of the massage units 102-1 to 102-n integrated in the seat 103 are activated by means of the output signal 107 based on the entertainment signal 104. For example, a user of the seat 103 can himself choose the regions which are intended to be massaged by the massage units 102-1 to 102-n, for example the back or legs. In addition, multi-channel music playback, for example stereo or 5.1, can be reproduced by means of the output signal 107 based on the entertainment signal 104.

Preferably, only some of the massage units 102-1 to 102-n integrated in the seat 10 are activated simultaneously by means of the output signal 107 based on the entertainment signal 104. For this purpose, a control device 106 distributes the levels for activating the massage units 102-1 to 102-n such that not all the massage units 102-1 to 102-n provided in the seat 103 simultaneously react to a level. Instead, the control apparatus 106 distributes the levels such that the massage units 102-1 to 102-n alternate, and the motors thereof can thus be held for a predetermined second period of time, for example in order to be cooled. Preferably, the cooling phases of individual massage units 102-1 to 102-n can be harmoniously integrated in the massage sequence such that the alternation of the massage units 102-1 to 102-n is imperceptible to the occupant.

Finally, the acoustic entertainment signal 104 can be used as an input variable for the activation, in particular irrespective of an output volume set on the playback device 105. With an embodiment of this kind, it is possible for example to guess songs on the basis of the massage if the output volume is set to zero. Of course, the acoustic entertainment signal 104 can however also be adapted depending on the output volume of the playback device 105. The output volume thus determines the intensity of the vibrations in an embodiment of this kind.

In one embodiment, a diode can be arranged in the signal path, thus in a connection between the playback device 105 and the control device 106. The diode is in this case used as a rectifier device, and therefore only positive signal components are transmitted to the massage units 102-1 and 102-2.

Figure 2:
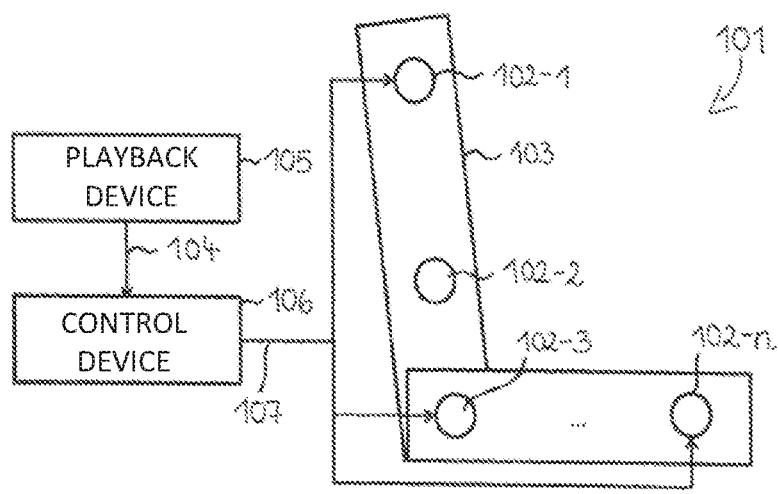
FIG. 2 is a block diagram of one embodiment of the seat arrangement according to the invention.

FIG. 2 is a block diagram of one embodiment of the seat arrangement 101 according to the invention.

A number of, thus one or more, massage units 102-1 to 102-n, in this case specifically four, are arranged in the seat 103. In FIG. 2, the massage units 102-1 and 102-2 are arranged in the seat back and the massage units 102-3 and 102-n are arranged in the sitting surface simply by way of example. Additional massage units are indicated by three dots. The number and arrangement of the massage units can vary depending on the application.

A control device 106 is provided for activating the massage units 102-1 to 102-n, which device generates a control signal 107 for the massage units 102-1 to 102-n from an entertainment signal 104 provided by a playback device 105, and forwards said control signal to said units.

The entertainment signal 104 may be for example an audio signal, which is a piece of music or the like. The entertainment signal 104 can come from various sources in this case. For example, the playback device 105 can be an audio system installed in a vehicle, comprising a radio or CD player. The playback device 105 can, however, also be the audio system for example, which receives the entertainment signal 104 from e.g. a smartphone via bluetooth.

In particular, the control device 106 and the playback device 105 can be combined or integrated in a single appliance. For example, the control device 106 can already be integrated in the vehicle audio system. In one embodiment, the massage units 102-1 to 102-n are directly coupled to the playback device 105, which has the required activation circuit for providing the output signal 107. Both the playback device 105 and the control device 106 can in this case be designed, at least in part, as computer program modules that are executed by a computing apparatus of the audio system.

Figure 3:
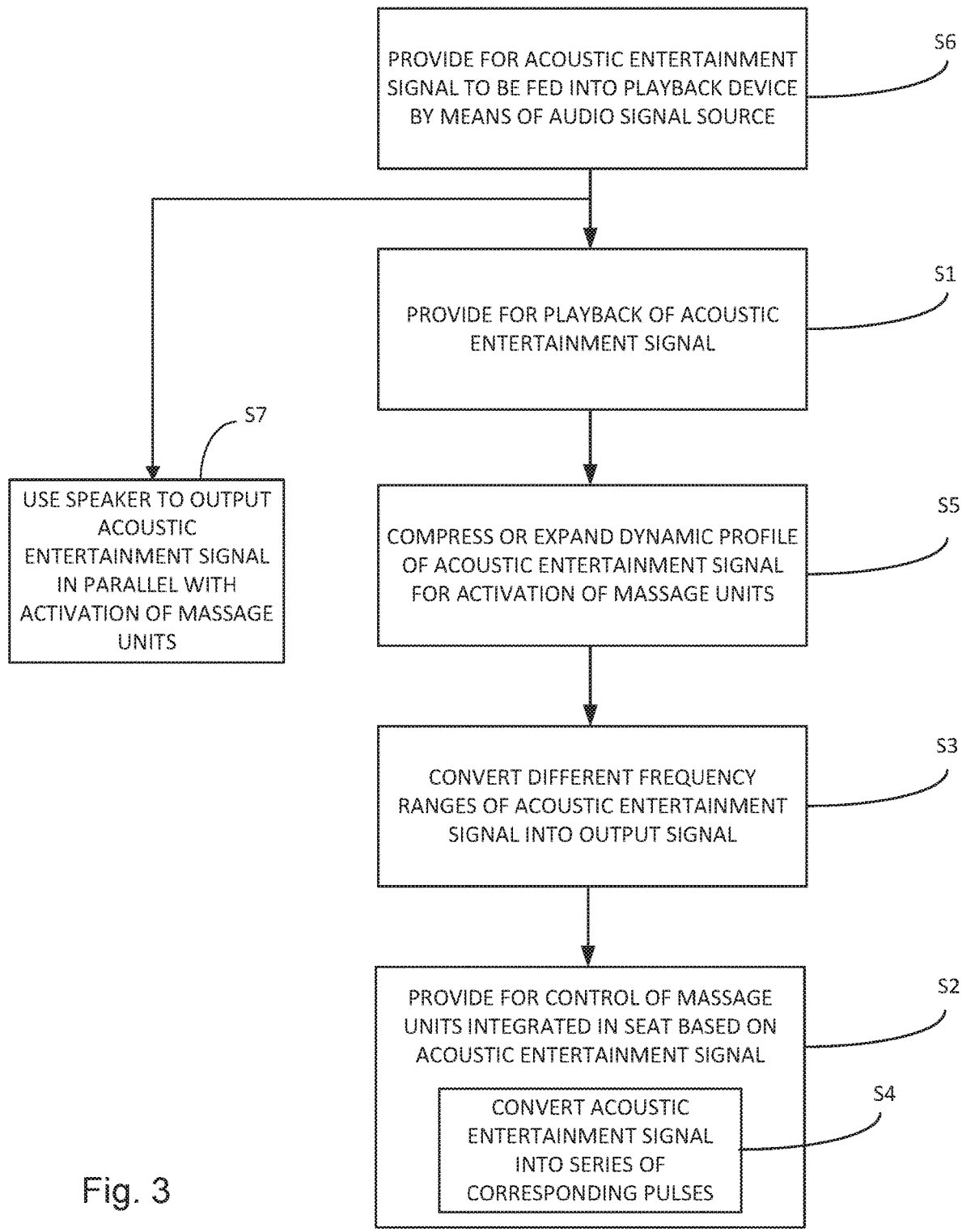
FIG. 3 is a flow diagram of a further embodiment of the method according to the invention.

FIG. 3 shows a flow diagram of a further embodiment of the method according to the invention. The method from FIG. 3 is based on the method from FIG. 1 and has additional steps, S3 to S7. The numbering of the individual steps S1-S7 is only used for differentiation and does not imply an order. In particular, individual steps can also be carried out at different positions from those disclosed in the following.

Step S6, before step S1, provides for the acoustic entertainment signal 104 to be fed into the playback device 105 by means of an audio signal source. In this case, the audio signal source can in particular be a mobile audio signal source, such as a smartphone or the like, or a vehicle-internal audio signal source, such as a CD player.

Following playback S1 of the acoustic entertainment signal 104, the dynamic profile of the acoustic entertainment signal 104 can be compressed and/or expanded, S5, for the activation of the massage units 102-1 to 102-n. The compression in this case is used in particular to limit the dynamic range of the acoustic entertainment signal 104, whereas the dynamic range of the acoustic entertainment signal 104 can be increased by means of the expansion. Following step S5, in step S3, different frequency ranges of the acoustic entertainment signal 104 are each converted into an output signal 107. For example, different massage units 102-1 to 102-n can be activated using signals having different frequencies. It can also be provided to allow the user to select the frequencies or the massage units 102-1 to 102-n to be activated using the respective frequencies. In particular, a type of equaliser can be displayed in a vehicle, e.g. in the head unit, i.e. a central display and control unit, which equaliser can be configured by the user. The massage units 102-1 to 102-n can in particular also be activated in groups for this purpose.

The massage units 102-1 to 102-n can in particular be activated by means of a pulse-width-modulated signal. For this purpose, in step S4, the acoustic entertainment signal 104 can be converted into a series of corresponding pulses, for example by means of a single high-side switch.

A speaker can output the acoustic entertainment 104 signal in parallel with the activation of the massage units 102-1 to 102-n, S7.

Figure 4:
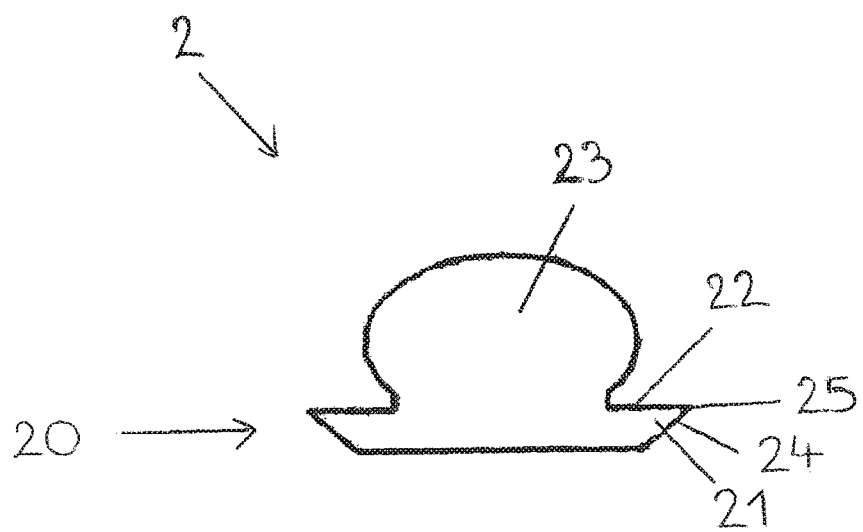
FIG. 4 shows a massage unit according to a first embodiment.

FIG. 4 shows a massage unit 2 according to a first embodiment. This can be used in the method and/or vehicle seat described with respect to FIGS. 1 to 3.

The massage unit 2 has a self-fastening design 20 when the massage unit 2 is inserted into a recess in a piece of upholstery.

In the present embodiment, the self-fastening design 20 is realised by means of a barb 21 that is integral with a housing 22 of the massage unit 2.

The barb 21 can be provided so as to surround the housing 22 or can be provided on said housing in regions. Said barb has an oblique end face 24 that projects laterally beyond the rest of the housing 22. The barb 21 also has a sharp edge 25 on the rear side thereof.

The massage units 2 also have a vibration generator 23 (not shown in detail for the sake of clarity) arranged inside the housing 22. The vibration generator 23 is used as the massage actuator and is for example an unbalance motor. A weight that is arranged on the armature shaft of an electric motor and is eccentric with respect to the axis of rotation of the electric motor is used in the case of the unbalance motor. Rotation of the motor results in a vibration. If a massage unit 2 is part of a massage device of a vehicle seat, a vibration of this kind can be transmitted to an occupant for example through a cover of the vehicle seat in the form of a massage.

Figure 5:
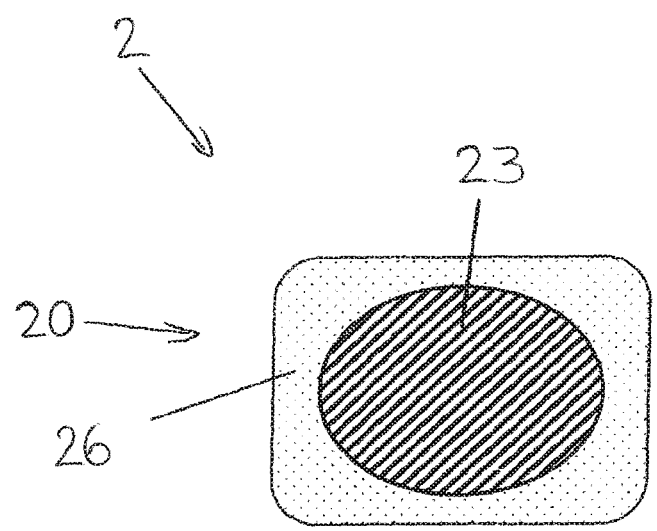
FIG. 5 shows a massage unit according to a second embodiment.

FIG. 5 shows a massage unit 2 according to a second embodiment. This can also be used in the method and/or vehicle seat described with respect to FIGS. 1 to 3.

In this embodiment, the self-fastening design 20 comprises embedding the massage unit in a foam cushion 26.

The foam of the foam cushion 26 has a very high coefficient of friction in a friction pairing with upholstery of a vehicle seat. On account of the high degree of friction, self-fastening of the massage unit can take place when the foam cushion 26 or the massage unit 2 together with the foam cushion 26 is introduced into a recess in a piece of upholstery.

Figure 6:
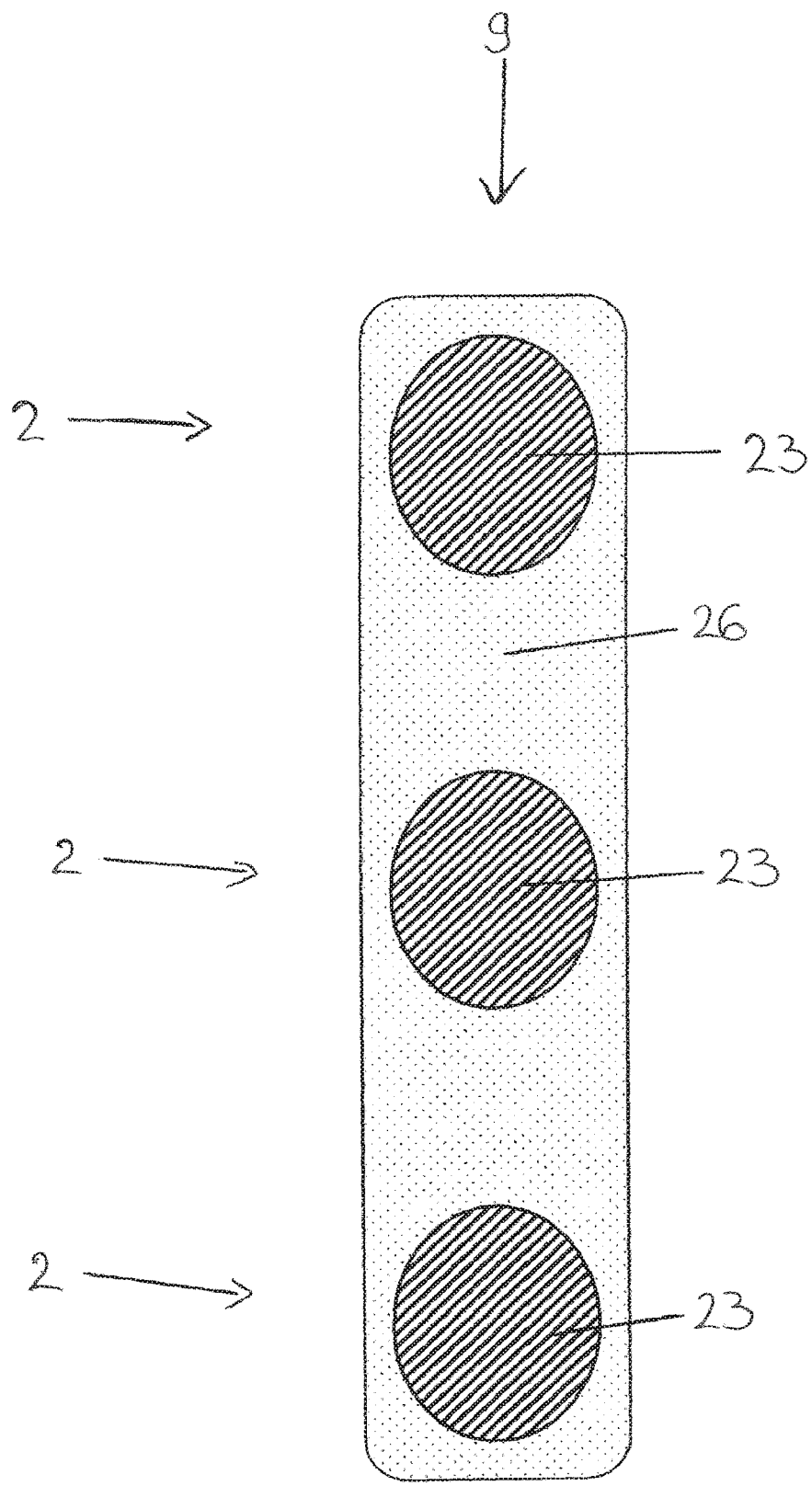
FIG. 6 shows a group of massage units according to the second embodiment.

FIG. 6 shows a group 9 of massage units 2 according to the second embodiment. In this case, this is a group 9 of three massage units 2 in a row that are embedded or foamed into a common foam cushion 26. Each massage unit 2 has a vibration generator 23 in this case. A group 9 of this kind can be integrated together in upholstery of a vehicle seat, as explained in more detail with respect to FIG. 15.

Figure 7:
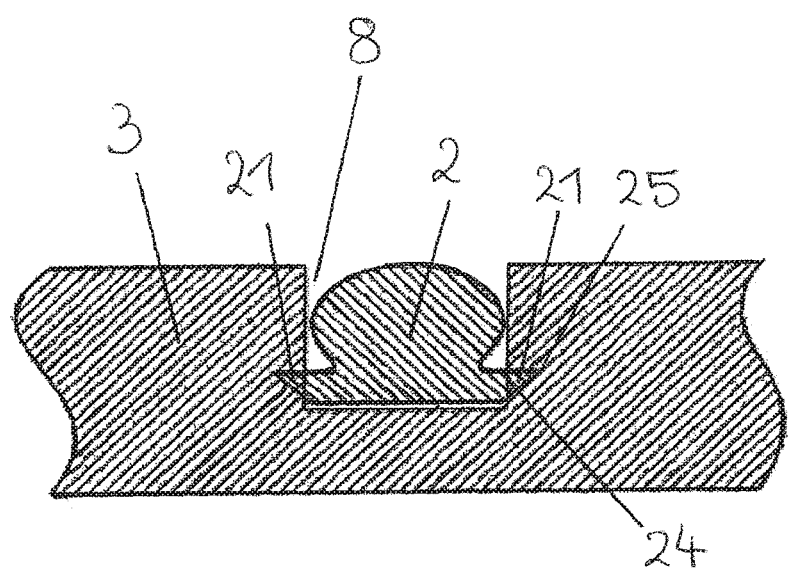
FIG. 7 shows the massage unit according to FIG. 4 in a recess in a piece of upholstery.

FIG. 7 shows the massage unit according to FIG. 4 in a recess 8 in a piece of upholstery 3.

The upholstery 3 can in particular be upholstery of a vehicle seat.

When the massage unit 2 is introduced into the recess 8 in the upholstery 3, the oblique end face 24 of the barb 21 slides along the material of the upholstery 3 such that the upholstery 3 is locally elastically deformed in the process. When the edge 25 forming the outermost portion of the barb 21 passes the upholstery 3, the upholstery 3 expands again therebehind. The edge 25 of the barb 21 thus digs into the upholstery 3 when the massage unit 2 moves out of the recess. Thus, once the massage unit 2 is introduced into the recess 8, it is automatically fastened or self-fastens therein.

Figure 8:
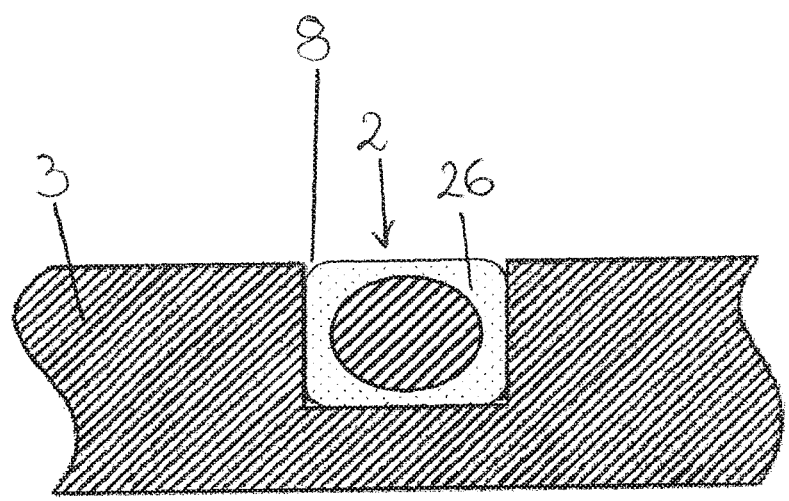
FIG. 8 shows the massage units according to FIG. 5 in a recess in a piece of upholstery.

FIG. 8 shows the massage unit 2 according to FIG. 5 in a recess 8 in a piece of upholstery 3.

The upholstery 3 can in particular be upholstery of a vehicle seat.

On account of the high coefficient of friction between the foam of the foam cushion 26 and the upholstery 3, self-fastening occurs when the massage unit 2 together with the foam cushion 26 is introduced into the recess 8 in the upholstery 3, as shown.

The frictional force and thus the self-fastening can be enhanced by the dimensions of the foam cushion 26 being tailored to the recess 8 by means of an oversize. There is then something of a pressing action between the foam cushion 26 and the recess 8, such that the adherence of the foam cushion 26 in the recess 8 is enhanced. For mounting, the foam of the foam cushion 26 is resiliently compressed by means of a corresponding tool, for example appropriately shaped pliers. After being introduced into the recess 8 and after the tool being released, the foam of the foam cushion 26 resiliently expands such that there is self-fastening of the massage unit 2 in the recess 8.

Figure 9:
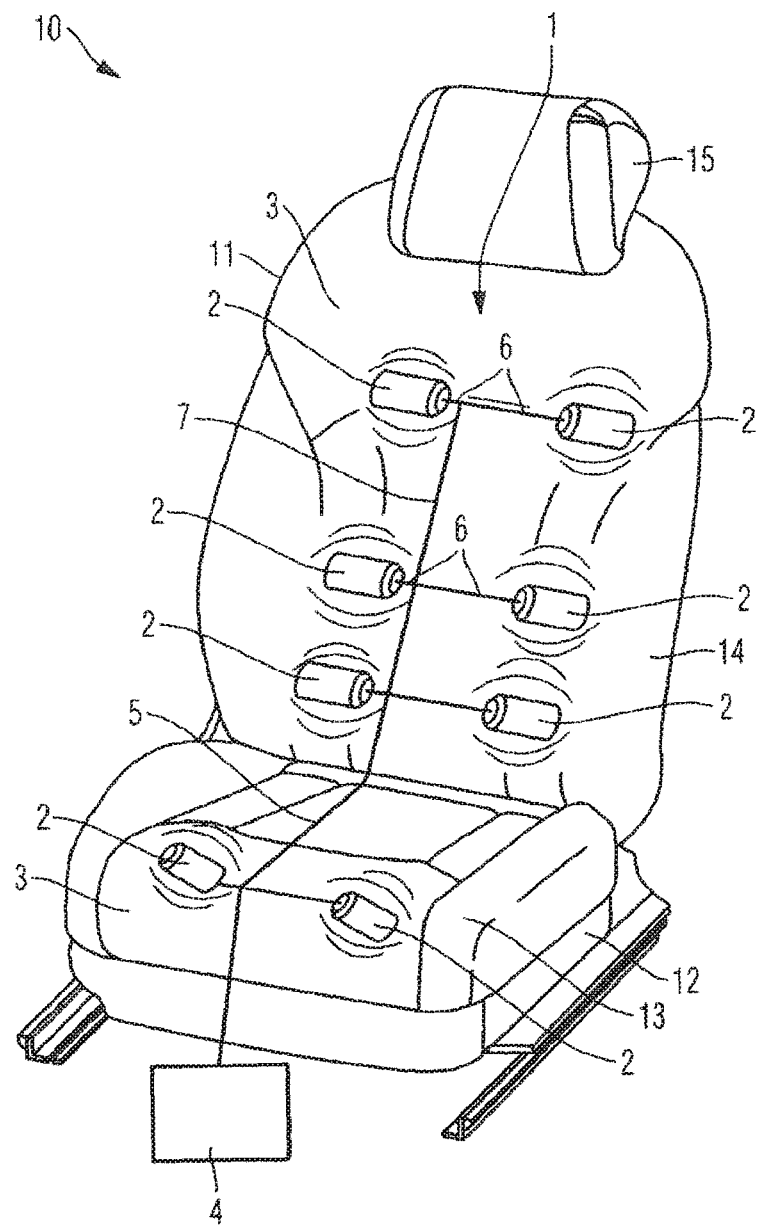
FIG. 9 shows a vehicle seat comprising a massage device according to a first embodiment.

FIG. 9 shows a vehicle seat 10 comprising a first embodiment of a massage device 1.

The vehicle seat 10 has a base 12 running in guide rails 16, a sitting surface 13, a backrest 14 and a headrest 15. Arm rests (not shown) may also be provided.

The massage device 1 is provided so as to be integrated in the vehicle seat 10. Said device has a plurality of massage units 2 that are integrated in the upholstery 3 of the vehicle seat 10. In the present embodiment, both the sitting surface 13 and the backrest 14 have upholstery 3 of this kind.

Furthermore, a control device 4 is provided, which is provided for and designed to activate all the massage units 2. This may be for example a computing device comprising a corresponding computer program, or a controller that provides the individual massage units with suitable control signals. In particular, the control device 4 and a playback device can be combined or integrated in a single appliance. For example, the control device 4 can already be integrated in the vehicle audio system. In this case, the control device 4 can be designed, at least in part, as a computer program module that is executed by a computing apparatus of the audio system.

The control device 4 can also be coupled to a human-machine interface, for example an additional button panel or a touchscreen operating module, or to the operating unit of an entertainment system of a vehicle, by means of which interface an occupant can operate the massage device 1.

A connection apparatus 5 is also provided, which couples the control device 4 to the massage units 2. For this purpose, the connection apparatus 5 has a cable harness 7 in which at least one cable 6 is packaged for each massage unit 2. The cables 6 branch off from the cable harness 7 at the relevant points, in particular in the region of the massage units 2 assigned thereto and, when fitted, come into contact with the relevant massage unit 2.

The cable harness 7 extends laterally or asymmetrically in the upholstery 3 rather than centrally. In addition, the cables 6 branching off in the same region have different lengths. The connection apparatus 5 is thus asymmetrical.

Consequently, a predetermined cable 6 is assigned to the predetermined position of each massage unit 2 and is provided with an individual cable length so that it can be laid only in said predetermined position of the relevant massage unit 2, in particular without shortening or lengthening the cable. If a cable 6 were to be laid in a different position of a different massage unit 2, to which it has not been assigned, it would be too short or too long and thus would not fit this different position. In such a case, the incorrect position would be indicated to a worker laying the cable 6 as a result of the unsuitable cable length.

The cable harness 7 is brought into contact with the control device 4 centrally. For this purpose, for example an asymmetrical plug having a predetermined pinout can be provided, which plug lays the cables 6 that are predetermined for the individual massage units 2 on likewise predetermined pins. The asymmetrical arrangement of the cables 6 is thus also reproduced when connecting the control device 4, by means of the asymmetrical plug. Accordingly, the control device 4 thus has a corresponding asymmetrical counter plug. It is thus ensured that there is correct contacting/plugging-in between the cable harness 7 and the control device 4.

In accordance with the asymmetrical or non-central arrangement of the cable harness 7, the control device 4 is also arranged asymmetrically or non-centrally on the vehicle seat 10.

In contrast with the connection apparatus 5, the massage units 2 are integrated so as to be distributed symmetrically on the relevant upholstery 3. An individual cable length is assigned in this case to each massage unit 2. This is specified by the position or arrangement of a recess 8 assigned to the relevant massage unit 2.

The massage units 2 are individual massage units 2 in the embodiment shown. The control device 4 controls the rotational speed of the unbalance motors of the massage units 2 and thus the vibration frequency thereof. Accordingly, the control device 4 can play back a massage program in which the various massage units 2 are appropriately activated to provide a massage. This can take place in particular according to a method described with respect to FIGS. 1 to 3.

In the embodiment shown, the control device is arranged outside of the vehicle seat 10. This is purely schematic, however. In other embodiments, the control device 4 can also be integrated in the vehicle seat 10, for example in the base 12 thereof or in the upholstery 3.

In order to mount the massage device 1 in the vehicle seat 10, the massage units 2 are brought into contact with the cables 6 of the connection apparatus 5 that are assigned thereto, and are inserted into the recess 8 assigned thereto in each case. In the process, either the contacting can take place first, followed by the insertion, or the insertion can take place first, followed by the contacting. The insertion and contacting of the massage units 2 take place separately in each case.

In a subsequent production step, the upholstery 3 is overlaid with the cover 11. When mounted, the massage units 2 are thus upholstered, in particular completely.

Figure 10:
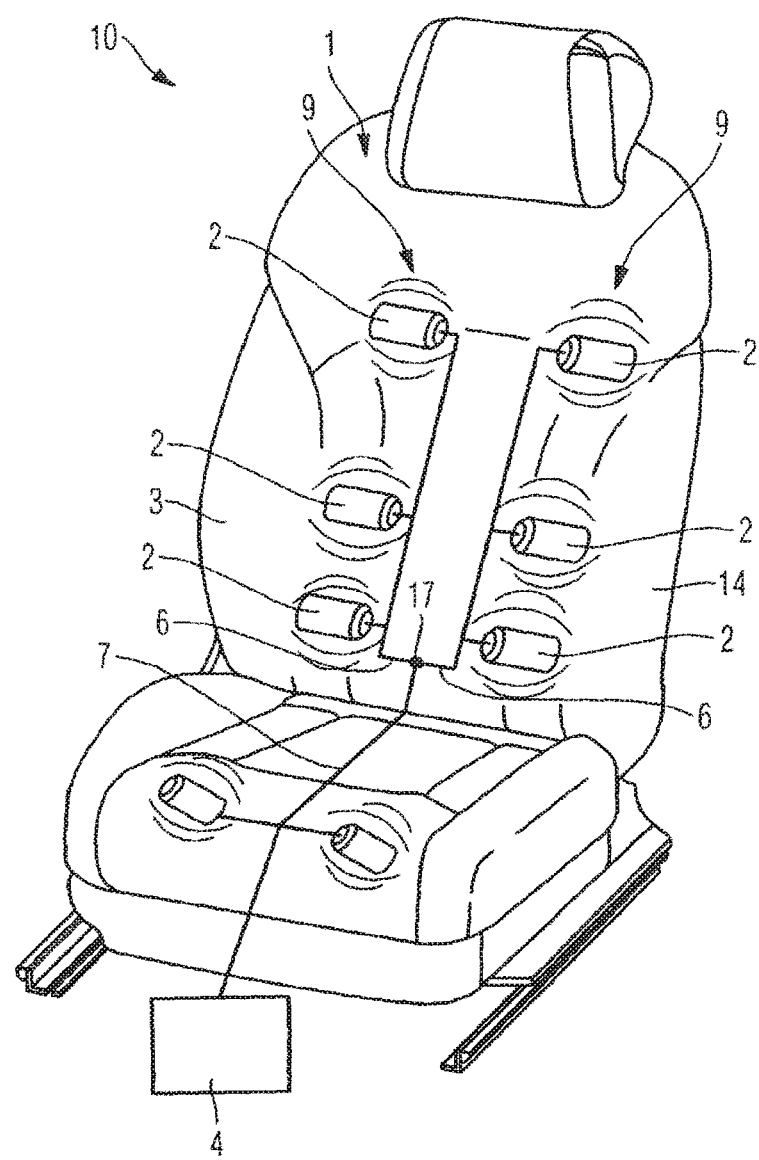
FIG. 10 shows a vehicle seat comprising a massage device according to a second embodiment.

FIG. 10 shows a vehicle seat comprising a massage device according to a second embodiment.

In contrast with the first embodiment of the massage device 1 according to FIG. 9, in this second embodiment, the massage units 2 are arranged and contacted or cabled in groups 9. For this purpose, the groups 9 are preassembled or pre-cabled before the massage units 2 are mounted. In the embodiment shown, this means that, for the purpose of integration in the left-hand side of the upholstery 3 of the backrest 14, a first group 9 of three massage units 2 is already brought into contact with a first common connection cable 6 before mounting. Said common connection cable 6 is guided towards the centre of the vehicle seat 10, during mounting, before or after the massage units 2 have been inserted and, in this position, said cable is coupled to the cable harness 7 of the connection apparatus 5. Analogously, a second group 9 of three massage units 2, which are provided for integration in the right-hand side of the upholstery 3 of the backrest 14, are inserted into the right-hand side of the upholstery 3 and are coupled to the cable harness 7 of the connection apparatus 5 by means of a common connection cable 6.

The respective three massage units 2 of the left-hand and the right-hand group 9 are in each case predetermined for mounting at a predetermined height of the backrest 14. Said units are provided with a cable length corresponding to said predetermined mounting height, and therefore, proceeding from a connection point 17 of the common connection cable 6 on the relevant side of the upholstery 3, there is only one recess that corresponds to the relevant cable length in the upholstery 3. The group 9 can thus be installed and brought into contact with the cable harness 7 only in the predetermined manner. An incorrect installation is thus effectively prevented.

Asymmetrical plugs are provided at the connection point 17 and at the connection cables 6, which plugs can be interconnected only in the predetermined contacting process. It is thus ensured that the connection cable 6 is brought into contact with the cable harness 7 correctly.

Figure 11:
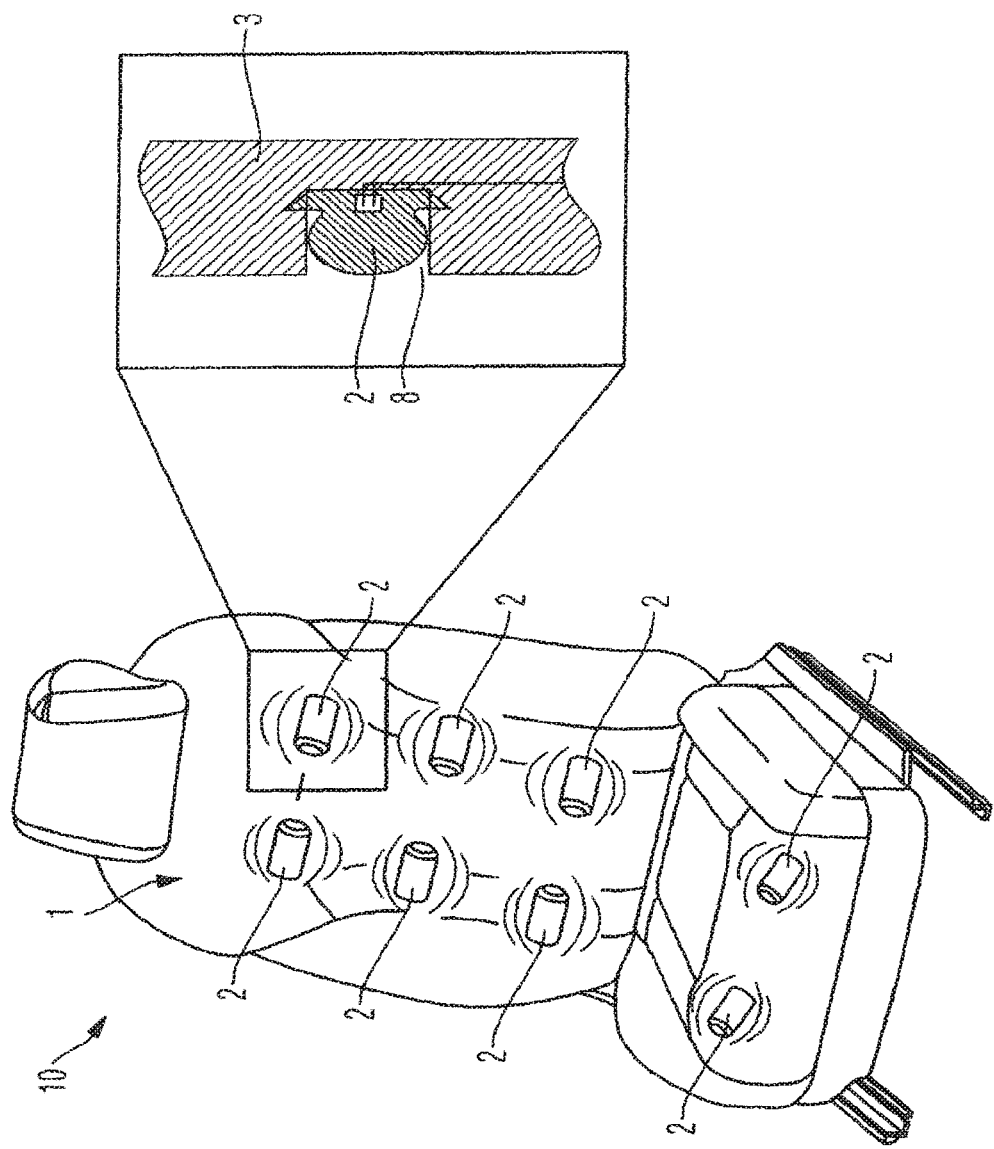
FIG. 11 shows a vehicle seat comprising a massage device having a plurality of massage units according to FIG. 4.

FIG. 11 shows a vehicle seat 10 comprising a massage device 1 having a plurality of massage units 2 according to FIG. 4; The massage units 2 are inserted into recesses 8 in the upholstery 3 at predetermined points on the upholstery 3 in the manner described with respect to FIG. 7.

This can be the first embodiment of a massage device 1 according to FIG. 9 comprising individual massage units 2, or the second embodiment of a massage device 1 according to FIG. 10 comprising massage units 2 that are preassembled and/or pre-cabled in groups 9.

Figure 12:
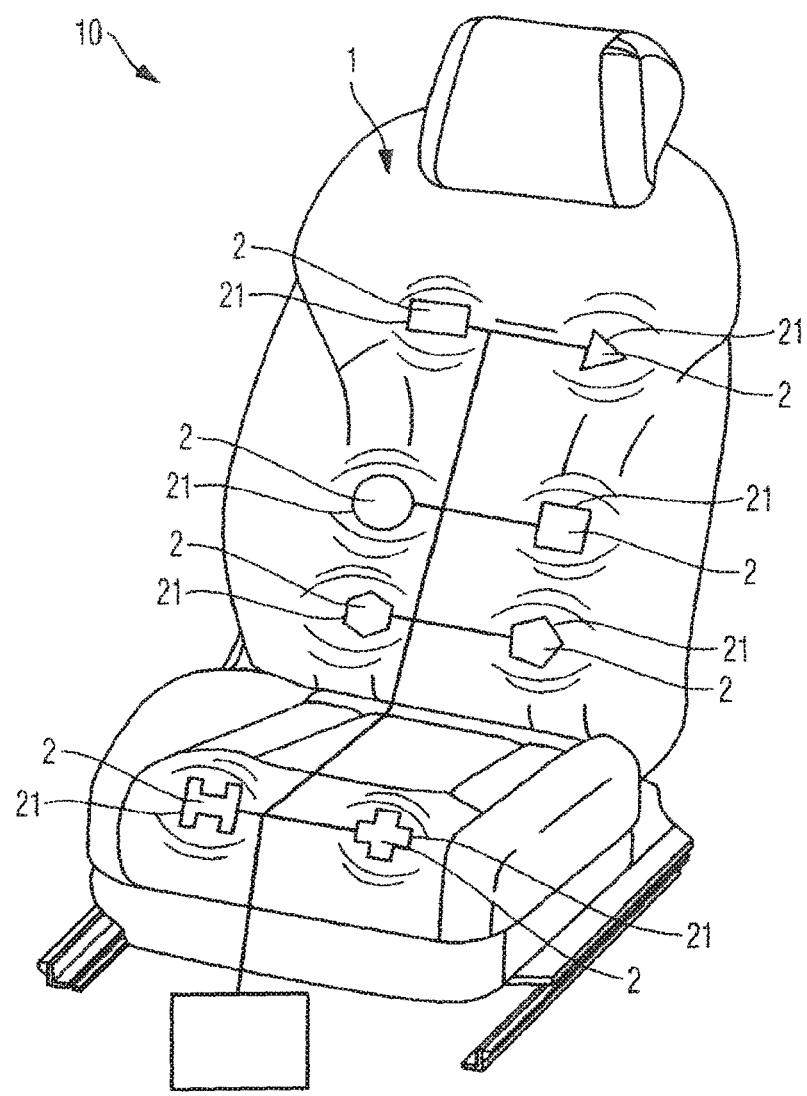
FIG. 12 is a schematic view of a massage device integrated in a vehicle seat, which device has shape-coded massage units.

FIG. 12 is a schematic view of a massage device 1 integrated in a vehicle seat 10, which device has shape-coded massage units 2.

In addition, each massage unit 2 has a housing 21 having an individual shape. Accordingly, each of the shape-coded massage units 2 is designed and provided so as to be inserted into a correspondingly shape-coded recess 8 in the upholstery 3 of the vehicle seat 10.

Figure 13:
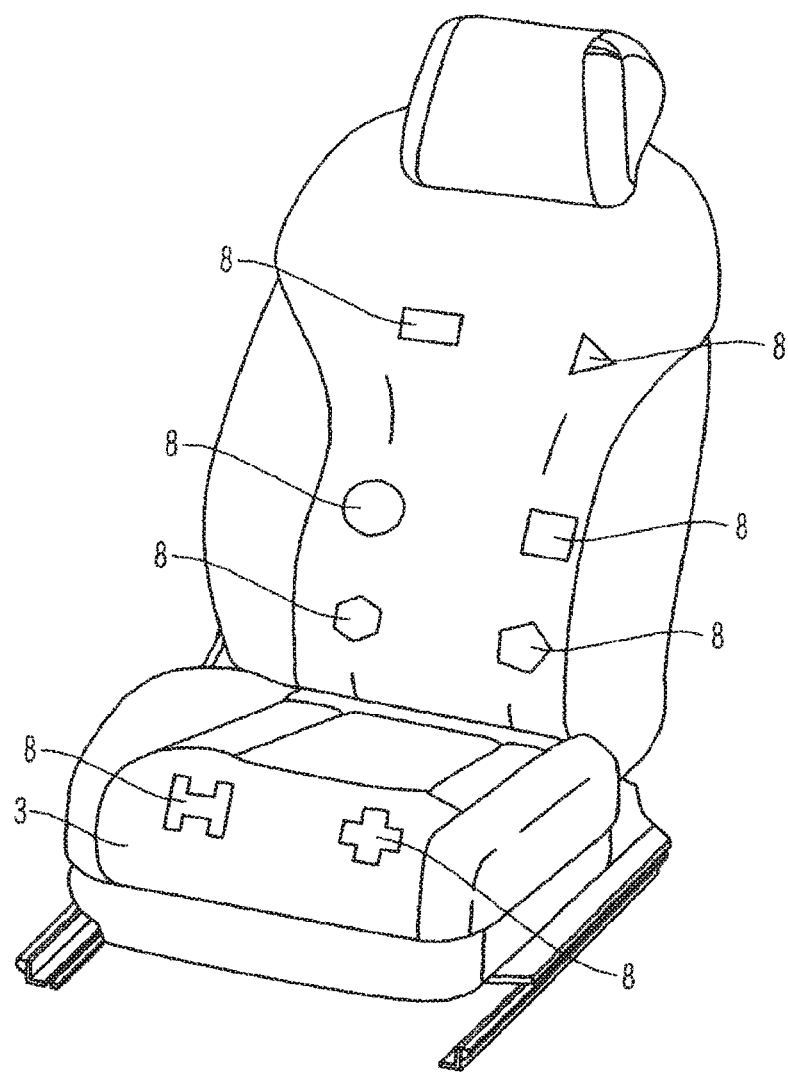
FIG. 13 shows upholstery of a vehicle seat comprising shape-coded recesses.

FIG. 13 schematically shows upholstery 3 of a vehicle seat 10 comprising shape-coded recesses 8 of this kind. Here, in each case only one recess 8 within the upholstery 3 has a shape that corresponds to the individual shape of a housing 21 of a shape-coded massage unit 2. It is thus ensured that only mutually corresponding massage units 2 and recesses 8 can be fitted together. Compliance with predetermined positioning of the shape-coded massage units 2 in the upholstery 3 is thus ensured during mounting.

Similarly, corresponding colour-coding, i.e. colouring housings 22 of the massage units 2 and colouring recesses 8 in the upholstery 3, can also be provided instead of or in addition to corresponding shapes. The colour-coding can also be extended to the cables 6 of the connection apparatus 5, such that for example differently coloured cables 6 and correspondingly coloured slots in the upholstery 3 for laying said cables are provided.

Shape-coding and/or colour-coding of this kind is expedient in particular if different massage units 2 are provided for different positions on the upholstery 3, for example for different regions of the backrest 14 and/or for seat upholstery 13 and the backrest 14 and/or for the left-hand side and the right-hand side.

Figure 14:
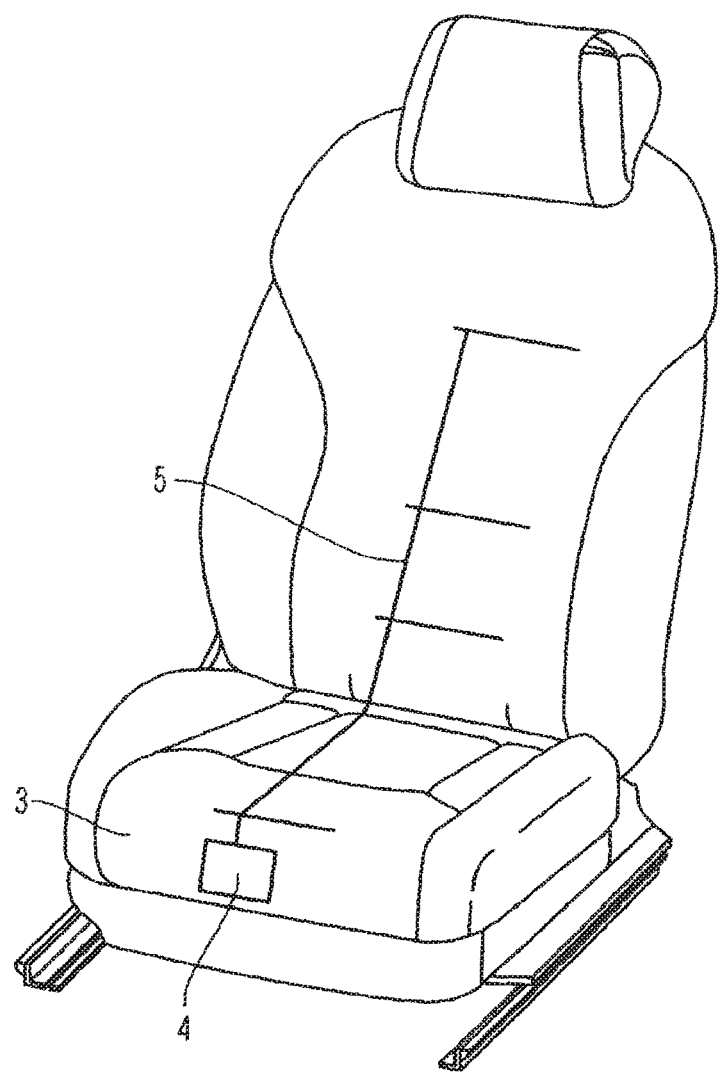
FIG. 14 is a schematic view of a connection element that is foamed into upholstery of a vehicle seat.

FIG. 14 is a schematic view of a connection element 5 that is foamed into upholstery 3 of a vehicle seat 10.

In the embodiment shown, the control device 4 is also provided so as to be foamed into the upholstery 3, in addition to the connection apparatus 5. The upholstery 3, the connection apparatus 5 and the control device 4 thus form a prefabricated or preassembled mounting module.

For the final mounting of the massage device 1, the massage units 2 are inserted into the recess 8 (not shown here) in the upholstery 3 and are brought into contact with the connection apparatus 5. The upholstery 3, together with the massage units 2, the connection apparatus 5 and the control device 4, are covered with the cover 11 or said cover is stretched thereover. Thus, when the massage device 1 is finally mounted in the vehicle seat 10, the connection apparatus 5, the massage units 2 and the controller 4 are upholstered as well.

Figure 15:
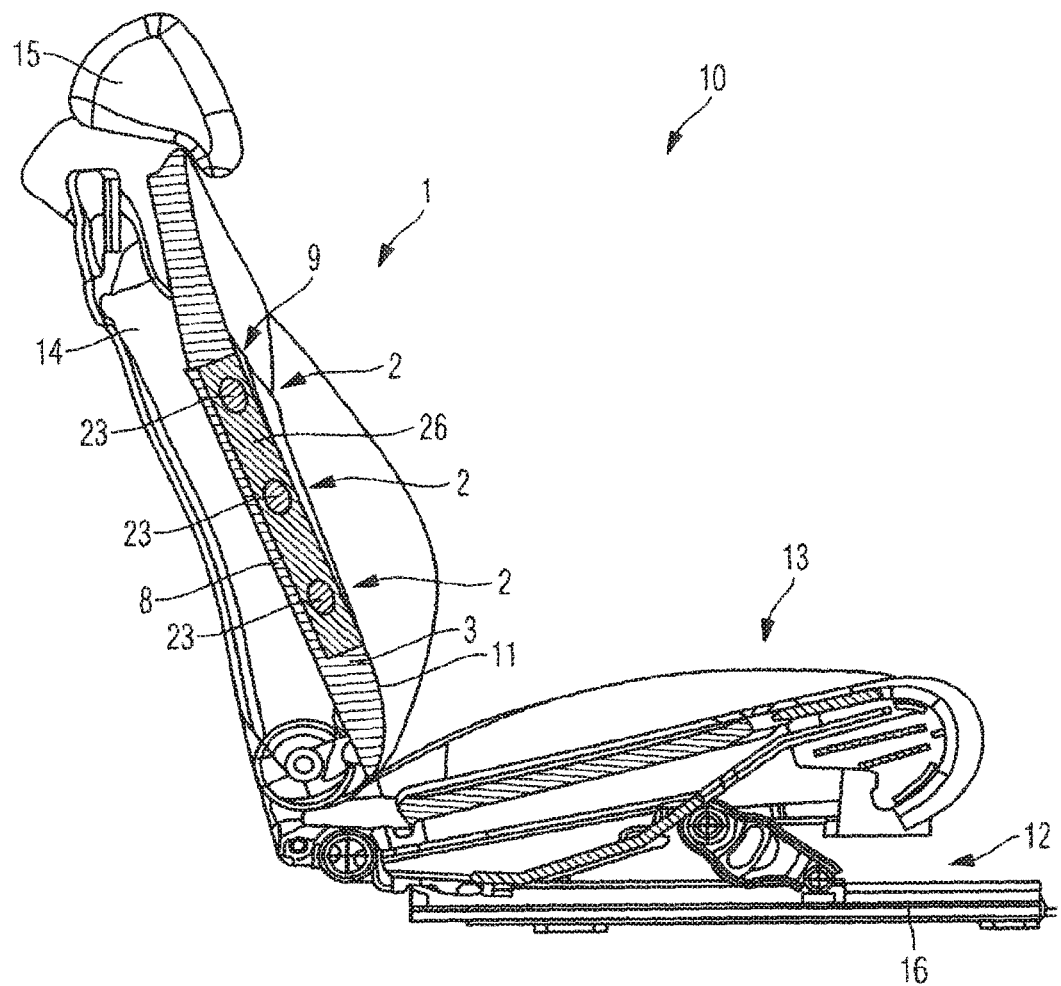
FIG. 15 is longitudinal sectional view of a vehicle seat comprising a massage device having a group of massage units according to FIG. 6.

FIG. 15 is a longitudinal sectional view of a vehicle seat 10 comprising a massage device 1 having a group 9 of massage units 2 according to FIG. 6.

The group 9 of massage units 2 is provided so as to be integrated in the backrest 14 of the vehicle seat 10. The group 9 of three massage units 2 shown here self-fastens, by stiction, in a recess 8 provided for said units within the upholstery 3 of the backrest 14. On account of a high coefficient of friction between the foam of the foam cushion 26 and the upholstery 3, self-fastening occurs when the group 9 of massage units 2 together with the foam cushion 26 is introduced into the recess 8 in the upholstery 3, as shown.

Analogously to the embodiment according to FIG. 8 comprising an individual massage unit 2, the friction force and thus the self-fastening of a group 9 can also be enhanced by the dimensions of the foam cushion 26 being tailored to the recess 8 in the upholstery 3 of the backrest 14 by means of an oversize.

Figure 16:
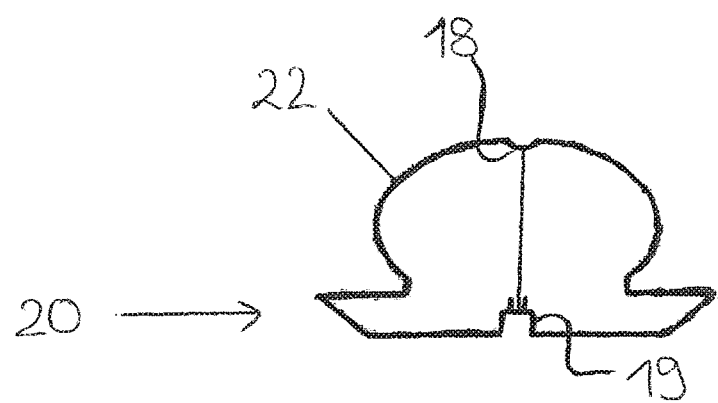
FIG. 16 shows one embodiment of a housing for a massage unit.

FIG. 16 shows one embodiment of a housing 22 for a massage unit 2.

The housing 22 has two halves, which are interconnected by means of a film hinge 18. The housing 22 is thus made in one piece. The housings 22 are injection-moulded parts. A plug 19 that is injection-moulded simultaneously is also provided. In the embodiment shown, each half of the housing 22 also forms a half of the plug 18.

In order to manufacture a massage unit 2, a vibration generator 23 is fitted in the housing 22 such that said generator can be contacted by means of the plug 19. The two halves of the housing 22 are then joined together by the film hinge 18 being folded.

If a force acts on the self-fastening design 20 that presses the two halves together, the plug 19, as shown here, is joined together in its intended form. The two halves can also be fastened to one another, in particular clipped, screwed or welded.

In the joined-together design of the housing 22, a connection apparatus 5 can then be brought into contact with the plug 19.

Although the present invention has hitherto been described entirely by way of preferred embodiments, it is not restricted thereto, but can be modified in various ways.

It goes without saying that the seat 103 can be arranged not only in a vehicle, but said seat 103 can also be e.g. an aircraft seat, a seat on a train or bus, or similar. If the present invention is used comprising a plurality of seats 103, a separate control device 106 may be provided for each of the seats 103. This is advantageous in particular if each seat 103 is provided with its own playback device 105. This is the case for example in aircraft or on trains, where headphone jacks are arranged on each seat, and a user can select an audio channel to which he wishes to listen. Alternatively, however, a central control device 106 which activates all the seats 103 can also be provided.

In addition, the groups 9 according to FIGS. 6 and 15, respectively, can be preassembled in a foam cushion 26 and can also be pre-cabled according to FIG. 10.

Analogously to the backrest 14 according to FIG. 15, groups 9 of massage units can also be provided so as to be integrated in the seat upholstery 13.

LIST OF REFERENCE SIGNS 1 massage device
2 massage unit 3 upholstery
4 control device
5 connection apparatus
6 cable
7 cable harness
8 recess
9 group
10 vehicle seat
11 cover
12 base
13 seat surface
14 backrest
15 headrest
16 guide rail
17 connection point
18 film hinge
19 plug
20 self-fastening design
21 barb
22 housing
23 vibration generator
24 oblique end face
25 edge
26 foam cushion
101 seat arrangement
102-1 to 102-*n* massage units
103 seat
104 entertainment signal
105 playback device
106 control device
107 output signal
S1-S7 method steps

The invention claimed is:

1. A method for activating a plurality of massage units integrated in a vehicle seat, comprising the following steps:
playing back an acoustic entertainment signal having a dynamic range, via a playback device of a vehicle; and
controlling the plurality of massage units based on the acoustic entertainment signal via a control device;
said step of controlling the plurality of massage units comprising:
converting the acoustic entertainment signal into at least one output signal; and
inputting each of the at least one output signal to an associated massage unit of the plurality of massage units for activating the associated massage unit of the plurality of massage units; wherein
said step of converting the acoustic entertainment signal into at least one output signal further comprises:
compressing the dynamic range of the acoustic entertainment signal for dynamic compression of the dynamic range of the acoustic entertainment signal and limiting the dynamic range of the acoustic entertainment signal, wherein
said step of controlling the plurality of massage units further comprises:
splitting the acoustic entertainment signal into a plurality of predetermined frequency ranges each having a dynamic range; and
said step of converting the acoustic entertainment signal into at least one output signal further comprises:
compressing the dynamic range of the acoustic entertainment signal in at least one predetermined frequency range of the plurality of predetermined frequency ranges for dynamic compression of the dynamic range in the at least one predetermined frequency range and limiting the dynamic range in the at least one predetermined frequency range to thereby generate the at least one output signal.

2. The method as claimed in claim 1, wherein said step of converting the acoustic entertainment signal into at least one output signal further comprises:
compressing the dynamic range of the acoustic entertainment signal in each one of the plurality of predetermined frequency ranges for dynamic compression of the dynamic range in each one of the plurality of predetermined frequency ranges and limiting the dynamic range in each one of the plurality of predetermined frequency ranges to thereby generate a plurality of output signals for activating the associated massage unit of the plurality of massage units.

3. The method as claimed in claim 2, wherein the plurality of massage units is arranged so as to be distributed over a sitting surface of the vehicle seat, and each one of the plurality of output signals is assigned to a different predetermined frequency range of the acoustic entertainment signal and is output to different ones of the plurality of massage units for activating massage units that are arranged in different places of the vehicle seat.

4. The method as claimed in claim 1, wherein only some massage units of the plurality of massage units integrated in the seat are activated via the output signal based on the acoustic entertainment signal.

5. The method as claimed in claim 1, wherein amplification and selection of different frequency ranges are provided that are in both cases adapted to the type of acoustic entertainment signal.

6. The method as claimed in claim 1, wherein the acoustic entertainment signal is used as an input variable for the activation, irrespective of an output volume set on the playback device.

7. The method as claimed in claim 6, wherein the intensity of the massage provided by the massage units or the vibration intensity of the massage units can be freely set.

8. The method as claimed in claim 1, wherein the acoustic entertainment signal is converted into a series of pulses for the activation of the massage units.

9. The method as claimed in claim 1, wherein the acoustic entertainment signal is fed into the playback device via an audio signal source or a vehicle-internal audio signal source.

10. The method as claimed in claim 1, wherein the massage units can be activated so as to vibrate in frequency ranges in which they only bring about noise emissions which are externally imperceptible to persons other than those sitting on the seat in question.

11. The method as claimed in claim 1, wherein the massage units are arranged and activated such that the vibration thereof covers or neutralises adjustment noise that is simultaneously generated by an electromotive seat adjustment.

12. The method as claimed in claim 1, wherein a speaker outputs the acoustic entertainment signal in parallel with the activation of the massage units.

13. A control device for controlling and activating a plurality of massage units integrated in a vehicle seat,
which control device is configured to convert an acoustic entertainment signal having a dynamic range into at least one output signal, and
which control device is further configured to activate the plurality of massage units in accordance with a method the method comprising the following steps:
playing back an acoustic entertainment signal having the dynamic range via a playback device; and controlling the plurality of massage units based on the acoustic entertainment signal via a control device;
said step of controlling the plurality of massage units comprising:
converting the acoustic entertainment signal into at least one output signal; and
inputting each of the at least one output signal to an associated massage unit of the plurality of massage units for activating the associated massage unit of the plurality of massage units; wherein
said step of converting the acoustic entertainment signal into at least one output signal further comprises:
compressing the dynamic range of the acoustic entertainment signal for dynamic compression of the dynamic range of the acoustic entertainment signal and limiting the dynamic range of the acoustic entertainment signal, wherein
said step of controlling the plurality of massage units further comprises:
splitting the acoustic entertainment signal into a plurality of predetermined frequency ranges each having a dynamic range; and
said step of converting the acoustic entertainment signal into at least one output signal further comprises:
compressing the dynamic range of the acoustic entertainment signal in at least one predetermined frequency range of the plurality of predetermined frequency ranges for dynamic compression of the dynamic range in the at least one predetermined frequency range and limiting the dynamic range in the at least one predetermined frequency range to thereby generate the at least one output signal.

14. The control device as claimed in claim 13, wherein
said step of converting the acoustic entertainment signal into at least one output signal further comprises:
compressing the dynamic range of the acoustic entertainment signal in each one of the plurality of predetermined frequency ranges for dynamic compression of the dynamic range in each one of the plurality of predetermined frequency ranges and limiting the dynamic range in each one of the plurality of predetermined frequency ranges to thereby generate a plurality of output signals for activating the associated massage unit of the plurality of massage units.

15. A vehicle seat arrangement comprising:
a vehicle seat, having a plurality of massage units integrated in the vehicle seat;
a playback device in of an entertainment system of a vehicle for playing back an acoustic entertainment signal; and a
control device coupled to the playback device for controlling the plurality of massage units based on the acoustic entertainment signal,
which control device is
configured to convert an acoustic entertainment signal having a dynamic range into at least one output signal, and
which control device is further configured to activate the plurality of massage units in accordance with a method the method comprising the following steps:
playing back an acoustic entertainment signal having the dynamic range via a playback device; and
controlling the plurality of massage units based on the acoustic entertainment signal via a control device;
said step of controlling the plurality of massage units comprising:
converting the acoustic entertainment signal into at least one output signal; and
inputting each of the at least one output signal to an associated massage unit of the plurality of massage units for activating the associated massage unit of the plurality of massage units; wherein
said step of converting the acoustic entertainment signal into at least one output signal further comprises:
compressing the dynamic range of the acoustic entertainment signal for dynamic compression of the dynamic range of the acoustic entertainment signal and limiting the dynamic range of the acoustic entertainment signal, wherein
said step of controlling the plurality of massage units further comprises:
splitting the acoustic entertainment signal into a plurality of predetermined frequency ranges each having a dynamic range; and
said step of converting the acoustic entertainment signal into at least one output signal further comprises:
compressing the dynamic range of the acoustic entertainment signal in at least one predetermined frequency range of the plurality of predetermined frequency ranges for dynamic compression of the dynamic range in the at least one predetermined frequency range and limiting the dynamic range in the at least one predetermined frequency range to thereby generate the at least one output signal.

16. The vehicle seat arrangement as claimed in claim 15, wherein
said step of converting the acoustic entertainment signal into at least one output signal further comprises:
compressing the dynamic range of the acoustic entertainment signal in each one of the plurality of predetermined frequency ranges for dynamic compression of the dynamic range in each one of the plurality of predetermined frequency ranges and limiting the dynamic range in each one of the plurality of predetermined frequency ranges to thereby generate a plurality of output signals for activating the associated massage unit of the plurality of massage units.

17. The vehicle seat arrangement as claimed in claim 15, wherein the massage units are configured as unbalance motors or, unbalance step motors, which can be operated in different frequency ranges.

18. The vehicle seat arrangement as claimed in claim 15, wherein a rectifier element is arranged in the motor supply line or in a connection between the playback device and the control device.

* * * * *